United States Patent [19]

Barnett et al.

[11] Patent Number: 4,997,771

[45] Date of Patent: Mar. 5, 1991

[54] METHOD FOR MEASURING THE BZ-1 RECEPTOR BINDING ACTIVITY IN A TEST SAMPLE OR TEST COMPOUND

[75] Inventors: Allen Barnett, Pine Brook; William Billard, Scotch Plains; Gordon Crosby, Jr., Hackensack; Louis Iorio, Lebanon; Martin Steinman, Livingston, all of N.J.

[73] Assignee: Schering Corporation, Kenilworth, N.J.

[21] Appl. No.: 43,111

[22] Filed: Apr. 27, 1987

[51] Int. Cl.$^5$ .................. G01N 33/566; C07D 243/24
[52] U.S. Cl. ...................................... 436/501; 436/503; 436/504; 436/804; 436/808; 436/816; 436/901; 424/1.1; 424/2; 435/4; 435/810; 540/504; 540/510; 514/249
[58] Field of Search ............... 436/501, 503, 504, 804, 436/808, 816, 901; 424/2, 1.1, 244; 540/504, 505, 510; 435/4, 810

[56] References Cited

U.S. PATENT DOCUMENTS 3,845,039 10/1974 Steinman ............................. 540/505
4,239,744 12/1980 Paul et al. ........................ 436/504 X
4,760,029 7/1988 Barnett et al. ....................... 436/504

OTHER PUBLICATIONS

Sieghart, W., Neuroscience Letters, 38, 73–78, (1983).
Iorio, L. C. et al., Life Sci., 35:105–113, (1984).
Corda, M. et al., Chem. Abstr., 105(13):1986, Abstract No. 109233r.
New England Nuclear Catalog, (1983), pp. 7–8 and 127.

Primary Examiner—Esther L. Kepplinger
Assistant Examiner—Carol A. Spiegel
Attorney, Agent, or Firm—Warrick E. Lee, Jr.; James R. Nelson; Norman Dulak

[57] ABSTRACT

The invention describes a method for determining the BZ-1 receptor activity of a test sample or a potential anxiolytic drug.

11 Claims, No Drawings

METHOD FOR MEASURING THE BZ-1 RECEPTOR BINDING ACTIVITY IN A TEST SAMPLE OR TEST COMPOUND

BACKGROUND OF THE INVENTION

A number of studies have indicated the existence of more than one type of benzodiazpine (BZ) receptor in brain [J. Parmacol. Exp. Ther., 221, 670 (1982), Pharmacol. Biochem. Behav., 11, 457 (1979), Pharmacol. Biochem. Behav., 10, 825 (1979), Nature, 286, 606 (1980), Nature, 286, 285 (1980), J. Parmacol. Exp. Ther., 212, 337 (1981)]. The evidence for this comes primarily from work with two classes of compounds: the triazolopyridazine and β-carbolines. These drugs exhibit shallow inhibition curves in competing for $^3$H-flunitrazepam or $^3$H-diazepam binding sites in various brain regions and also show regional selectivity (being more potent in cerebellum than in cortex or hippocampus).

One benzodiazepine (7-chloro-1-(2,2,2-trifluorethyl)-5-(2-fluorophenyl)-1,3-dihydro-2H-1,4 benzodiazpeine-2-thione) known as quazepam has been reported to display a receptor binding profile similar to that of the triazolopyridazine and β-carbolines described above [Life Sco., 35, 105 (1984), Neurosci. Lett., 38, 73 (1983)]. This compound displays a 54-fold difference in binding affinity for two BZ receptors (BZ-1 and BZ-2). A related benzodiazepine (7-chloro-1-(2,2,2-trifluorethyl)-5-(2-fluorophenyl)-1,3-dihydro-2H-1,4 benzodiazepine-2-one) known as 2-oxo-quazepam exhibited a 22-fold binding preference for the high affinity BZ receptor as well as an overall potency 14 times that of quazepam. In addition, 2-oxo-quazepam displays a much lower degree of non-specific binding (<5 percent at 0.5 nM).

2-oxoquazepam's high affinity for BZ-1 receptors together with minimal non-specific binding at low concentrations is a novel feature that makes labeled forms of this compound ideally suited for identifying and detecting other compounds that have BZ-1 specific activity.

SUMMARY OF THE INVENTION

One aspect of the present invention is a labeled form of the compound 7-chloro-1-(2,2,2-trifluoroethyl)-5-(2-fluorophenyl)-1,3-dihydro-2H-1,4 benzodiazepine-2-one (hereinafter referred to as 2-oxo-quazepam):

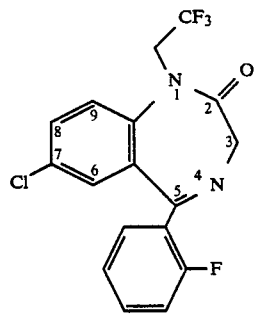

A preferred label of the invention is selected from an enriched level of radioactive atoms in order to facilitate the measurement of the relative binding affinity values, preferably an enriched level of tritium ($^3$H) atoms, and more preferably an enriched level of tritium ($^3$H) atoms attached to the α-carbon of the trifluoroethyl substituent located at the #1 position.

Another aspect of the invention is a method of determining the BZ-1binding activity of a test sample or test compound; said method comprising:

(a) supplying purified mammalian brain tissue containing BZ-1 receptors;
(b) adding labeled 2-oxo-quazepam to said mammalian brain tissue;
(c) adding a test compound or test sample to said mammalian brain tissue; and
(d) measuring the amount of label complexed with said BZ-1 receptors.

A first aspect of this method is determining the BZ-1 binding activity of a test sample or test compound as described above wherein the contact of mammalian brain tissue containing BZ-1 receptors is first made with the labeled compound, followed by the addition of the test sample or test compound. Whereas this first aspect would indicate BZ-1 binding activity of the test sample or test compound via a decreasing measurement of label, a second aspect of this method would indicate BZ-1 binding activity of the test sample or test compound via an increasing measurement label. This latter aspect would involve contacting mammalian brain tissue containing BZ-1 receptors to the test sample or test compound, followed by addition of labeled compound. In either method, comparison of label measurements to measurements of a standard would provide relative binding affinity for the test sample or test compound. The same results would not be obtained if the test sample or test compound was labeled instead of the 2-oxo-quazepam. Such labeled samples might bind to non-BZ-1 receptors and/or be susceptible to non-specific surface adhesion. Consequently, titrating to or with non-labeled 2-oxoquazepam in the presence of brain tissue containing BZ-1 receptors would result in displacement of only the BZ-1 bound samples, and an artificially low relative binding. Comparison to standards would not cure this problem since each labeled test sample or labeled test compound would have its own non-specific binding characteristics.

These methods measure the BZ-1 binding activity of either a test sample or test compound. A test sample may be obtained from the saliva, serum, urine or other bodily fluid. A test compound may be synthesized and/or purified from a natural source such as animal or plant tissue.

Another aspect of the invention is a kit for determining the level of BZ-1 binding activity of a test sample or a test compound; said kit comprising:

(a) a sample of purified mammalian brain tissue containing BZ-1 receptors; and
(b) a sufficient amount of labeled compound to determine the level of BZ-1 activity of said test sample or test compound.

DETAILED DESCRIPTION OF THE INVENTION 2-oxo-quazepam is a benzodiazepine that has potential clinical use as an anxiolytic, hypnotic, muscle relaxant and/or anticonvulsant as disclosed in U.S. Pat. No. 3,845,039 and U.S. Pat. No. 3,920,818. 2-oxoquazepam has also been reported to distinguish two subpopulations of benzodiazepine (BZ) receptors in Life Sc., 35, 105 (1984) and Neurosci. Lett., 38, 73 (1983). The significance of the two receptors may be related to different physiological effects. For example, Fed. Proc., 42, 344

(1983) discloses that the benzodiazepine, halazepam, had only weak ataxic effects in animals at doses far above tranquilizing doses. Similarly, quazepam caused only drowsiness and sleep in cats at doses below those that caused ataxia [Arzneim.-Forsch., 32, 1452 (1982), Arzneim.-Forsch., 32, 1456 (1982)].

Label is meant to include any marker attached or recognized on a molecule so as to confer an ability to distinguish that molecule from the unmarked or naturally occurring 2-oxo-quazepam. Examples of such labels include enzyme, fluorescent, luminescent, antibody and enriched levels of radioactivity. Titrating test samples or test compounds to or with the labeled 2-oxo-quazepam in the presence of brain tissue containing BZ-1 receptors will produce a competition binding profile, which when compared with a standard, will provide information about the BZ-1 binding activity of the test sample or test compound. This procedure will be useful for screening potential drugs for BZ-1 activity as well as determining the levels of BZ-1 activity in a serum, plasma or other test sample.

2-oxo-quazepam may be prepared from the corresponding 2,3-dihydrobenzodiazepine utilizing suitable oxidizing agents such as ruthenium tetraoxide and chromic trioxide as disclosed in U.S. Pat. No. 3,845,039, U.S. Pat. No. 3,920,818 J. Med. Chem., 16, 1354 (1973) or by other methods recognized in the art.

Labeling the 2-oxo-quazepam with an enzyme, fluorescent, luminescent, antibody, radioactive or tritium ($^3$H) label so as not to alter the binding properties of the receptor can be accomplished by techniques available in the art. As an example of a radioactive label, 2-oxo-quazepam may be tritiated at the α-carbon of the trifluoroethyl substituent located at the #1 position by reacting 7-chloro-5-(2-fluorophenyl)-1,3-dihydro-2H-1,4-benzodiazepine-2- with an appropriate trifluoroethylating agent that has been previously tritiated, e.g. $CF_3C(^3H)_2OSO_2C_4F_9$.

The utility of the labeled 2-oxo-quazepam and the method of using the labeled compound to determine the BZ-1 binding activity of a test sample or test compound is illustrated in the test procedures set forth below:

TISSUE PREPARATION

Male Spraque-Sawley rats (200 to 250 gms) from Charles River Breeding Laboratories, Mass., were used to obtain brain tissue. Animals were decapitated and their brains removed. Synaptic membranes were obtained following the procedure disclosed in Life Sc., 35, 105 (1984). Cerebral cortex and cerebellum were dissected on ice and homogenized in 20 volumes of ice cold 0.32 M sucrose using a glass homogenizer fitted with a teflon pestle. The homogenates were then centrifuged at 48,000 X g for 10 min, and the resultant P2 pellets were washed twice by re-centrifugation in 50 mM Na/K phosphate buffered saline (pH 7.4). The washed pellets were pooled and then resuspended in the same buffer to a final concentration of 50 mg of original tissue weight/ml.

ASSAY CONDITIONS

Total reaction mixture volume was 1 ml which included: (a) 100 μl of either $^3$H-flunitrazepam or $^3$H-2-oxo-quazepam (tritiated at the α-carbon of the trifluoroethyl substituent located at the #1 position), yielding a final concentration of 0.5 nM (b) 100 μl of various concentrations of competing drugs dissolved or suspended in 50 mM phosphate buffered saline (pH 7.4) containing 4 mg/ml methylcellulose (c) 800 μl of tissue homogenate diluted such that a total of 5 mg of tissue was present in the final reaction mixture. In each competition experiment 25 to 30 concentrations of drug were used to obtain a complete dose response curve.

Incubations were carried out at 0° C. for 90 minutes. Samples were then filtered under vacuum through 25 mm diameter Whatman GF/B filters on a Millipore 1225 Sampling Manifold and quickly washed with 3×5 ml of ice-cold PBS buffer. Filter-bound radioactivity was quantified through liquid scintillation counting following overnight solubilization of the receptor-radioligand complex in "Scintosol" scintillation cocktail (Isolab, Inc.).

COMPETITION CURVE ANALYSIS

Compound assisted curve fitting was conducted on an Apple IIe computer using a program described in Br. J. Pharmacol., 80, 582P (1983) and Trends in Pharmaceutical Sci., 5, 47, (1984). Enhancements were made to the program to allow disk storage of data and printing of the program to allow disk storage of data and printing of the graphics display. The program determines whether the results from individual competition experiments are best interpreted on the basis of a 1 or 2 site model and also provides the most probable proportions of radioligand bound to each of the sites.

Selection among models was made by comparing the sum of squares residual values for the best single and 2-site models and determining through a partial F-test evaluation whether 2-site modelling produced a statistically meaningful ($P<0.05$) improvement in fit as described in Anal. Biochem., 107, 220 (1980). If not, the best single site model was considered the model of choice.

RESULTS $^3$H-Funitrazepam vs. Quazepam or 2-Oxo-Quazepam

Flunitrazepam binds non-specifically to benzodiazepine receptors. Experiments in which quazepam and 2-oxo-quazepam were in competition with $^3$H-flunitrazepam for binding sites in rat cortex distinguished two subpopulations of $^3$H-flunitrazepam binding sites that were present in a relative proportion of 55 percent to 45 percent. For quazepam, the average difference in affinity for the two sites was 54-fold; for 2-oxo-quazepam it was 22-fold. In terms of relative affinities for benzodiazepine sites, 2-oxo-quazepam was at least 14 times more potent that quazepam. Competition of unlabeled flunitrazepam with $^3$H-flunitrazepam, however, revealed only a single uniform population of sites.

In rat cerebellum, which contains only BZ-1 sites, quazepam and 2-oxo-quazepam were found to complete quite differently for $^3$H-flunitrazepam binding sites. As expected, 2-oxo-quazepam did not distinguish subpopulations of binding sites in cerebellum. The average IC50 value (defined as the concentration of drug necessary to displace 50 percent of compound previously bound to a specific receptor type) of 8.8 nM obtained in this region was close to the IC50 value of 9.3 pM obtained for the high affinity component of 2-oxo-quazepam's binding in cortex.

$^3$H-2-Oxo-Quazepam vs. Quazepam or 2-Oxo-Quazepam

Saturation binding studies were conducted utilizing $^3$H-2-oxo-quazepam in rat cortex over a range of concentrations from 0.1 to 30 nM. The separation between specific and non-specific binding indicated the suitability of $^3$H-2-oxo-quazepam as a radioligand for benzodiazepine sites. Specific binding was defined as the difference between total binding and binding in the presence of 100 nM unlabeled clonazepam. At a concentration of 0.5 nM, non-specific binding for the radioligand constituted only 5 to 10 percent of total binding. As expected, non-specific binding displayed a linear relationship with increasing concentration even after saturation of BZ-1 receptors.

Results were obtained in rat cortex for quazepam and 2-oxo-quazepam when the competition experiments identical to those performed utilizing $^3$H-flunitrazepam were repeated using $^3$H-2-oxo-quazepam (0.5 nM) as the radioligand. In contrast to the 2-site curves of best fit obtained with $^3$H-flunitrazepam, all competition experiments with $^3$H-2-oxo-quazepam as the radioligand were best described with a single site curve fitting model. A comparison of the IC50 values obtained in both cortex and cerebellum indicates that 2-oxo-quazepam is roughly equipotent (IC50=16.8 nM in cortex, 13.6 nM in cerebellum) in competing with $^3$H-2-oxo-quazepam in these tissues. The corresponding IC50 values obtained with quazepam as the competing ligand were 101 nM in cortex and 258 nM in cerebellum. A comparison of the relative potentcies of quazepam and 2-oxo-quazepam indicates that 2-oxo-quazepam is 6 times more potent in cortex and 19 times more potent in cerebellum.

These data show that 2-oxo-quazepam, particularly at low concentrations (0.5 nM), binds BZ-1 receptors almost exclusively. When the labeled form of these two molecules is titrated with other suspected BZ-1 active compounds in the presence of brain tissue, the competitive binding profile, as evidenced by the decrease in measurement of the radioactive label, provides information about their amount and strength of binding activity when compared to similar binding profiles for known BZ-1 active compounds. Advantage may also be taken by the BZ-1 binding properties of labeled 2-oxo-quazepam to analyze for the presence and amount of BZ-1 binding activity in a test sample (plasma, serum, saliva, urine, etc.) obtained from a patient. For example, various dilutions of a sample are mixed with mammalian brain tissue (containing BZ-1 receptors) in the presence of a low concentration of labeled 2-oxp-quazepam. After incubation, the level of tissue bound label is determined for each concentration, a binding curve is constructed, and comparison is made to a binding curve for a known BZ-1 active compound.

In conclusion, labeled 2-oxo-quazepam is an excellent probe for studying the BZ-1 receptors in mammalian brains. They can be used to measure the BZ-1 binding activity of a test compound as well as the BZ-1 binding activity of a test sample. A kit containing the necessary components to perform the assays for competitive binding as described above, as well as a method to utilize such a kit to determine BZ-1 activity of a test compound or test sample would be a useful too. for evaluating potential anxiolytic drugs as well as patients exhibiting BZ-1 active effects.

EXAMPLES

The following examples serve to illustrate the present invention. Selection of labels, tissues, buffers, concentration of reagents and the values of other variable parameters are only to exemplify application of the present invention and are not to be considered as limitations thereof.

EXAMPLE I.

Preparation of
7-Chloro-1-$^3$H-(2,2,2-Trifluoroethyl)-5-(2-Fluorophenyl)-1,3-Dihydro-2H-1,4 Benzodiazepine-2-One Step 1. Preparation of [$^3$H]2,2,2-trifluoroethyl perfluorobutanesulfonate.

Sodium borotritide (41 mg, 1 mmol, 59.3 Ci) was added to a solution of ethyltrifluoroacetate (100 μl, 0.83 mmol) in 10 ml of dry THF and refluxed for 16 hours. The flask was cooled and the reaction treated dropwise with H$_2$SO$_4$ THF. The solution was distilled at $10^{-2}$torr and the distillate trapped in a U-tube at $-196°$ C. The contents of the U-tube were distilled through a short path still into a flask containing perfluorobutanesulfonyl fluoride (250 mg, 0.83 mmol). Triethylamine (125 μl, 0.83 mmol) was added and the solution was stirred for 1 hour. Ice water was added and the product extracted into CH$_2$Cl$_2$ (3×25 ml). The combined organic solutions were washed with H$_2$O (50 ml), dried over MgSO$_4$ and concentrated to 2 ml on a rotary evaporator. Toluene was added (25 ml) and the solution concentrated to 20 ml. The toluene solution of [$^3$H]2,2,2-trifluoroethyl perfluorobutanesulfonate was used directly in the next step.

Step 2. Preparation of
7-Chloro-$^3$H-(2,2,2-trifluoroethyl)-5-(2-fluorophenyl)-1,3-dihydro-2H-1,4-benzodiazepine-2-one.

7-chloro-5-(2-fluorophenyl)-1,3-dihydro-2H-1,4-benzodiazepine-2-one (30 mg, 0.1 mmol) and NaH (7 mg of 80 percent dispersion in mineral oil) were combined with 2ml dried DMF at 0° C. Toluene (5 ml) was added and the solution stirred for 2 hours at 0° C., 24 hours at ambient temperature and finally for 15 minutes at 45° C. The toluene solution of [$^3$H]trifluoroethyl perfluorobutanesulfonate was added and stirring continued at 45° C. for 4 hours. The solution was kept at room temperature overnight and then stirred at 45° C. for a further 4 hours. Ice water (25 ml) was added, the layers separated and the aqueous phase extracted with toluene (2×25 ml). The organic layers were pooled, washed with H$_2$O (25 ml), dried over MgSO$_4$ and evaporated to dryness. The residue was dissolved in CHCl$_3$ and purified on silica gel prep TLC plates. The plates were developed with CH$_2$Cl$_2$:EtOAc (85:15). The product was eluted into EtOAc. The EtOAc solution was evaporated to dryness and the final product dissolved in EtOH.

EXAMPLE II.

Kit For Determining the Level of BZ-1 Activity of a Potential Anxiolytic Drug or In a Mammalian Test Sample The kit may be prepared by providing:
(a) about 25–30 one ml incubation tubes containing 100 μl of $^3$H-2-oxo-quazepam which will yield a final concentration of 0.5 mM when diluted to 1.0 ml; and
(b) sufficient 800 μl aliquots of mammalian brain cortex tissue homogenate containing 5 mg of tissue each, prepared as described above.

EXAMPLE III.

Method for Determining the Level of BZ-1 Activity of A potential Anxiolytic Drug The method utilizes the kit described in Example II. For each competition experiment 25 to 30 concentrations of a drug are used to obtain a complete dose response curve. The final reaction mixture volume is 1.0 ml and contains:

(a) 100 μl of $^3$H-2-oxo-quazepam which will yield a final concentration f 0.5 nM when diluted to 1.0 ml;
(b) 800 μl of mammalian brain cortex tissue homogenate containing 5 mg of tissue;
(c) 100 μl of various concentrations of potential drug dissolved or suspended in 50 nM buffered saline (pH 7.4) containing 4 mg/ml methylcellulose.

Incubations are carried ut at 0° C. for 90 minutes. Samples are then filtered under vacuum through 25 mm diameter Whatman GF/B filters on a Millipore 1225 Sampling Manifold and quickly washed with 3×5 ml of ice-cold PBS buffer. Filter-bound radioactivity is quantified through liquid scintillation counting following overnight solubilization of the receptor-radioligand complex in "Scintosol" scintillation cocktail (Isolab, Inc.). The result is a counts per minute (CPM) value for each concentration of test drug assayed.

The CPM is corrected for non-specific binding of the $^3$H-2-oxo-quazepam by running a control assay tube without test drug in the absence of unlabeled 2-oxo-quazepam, and subtracting the CPM obtained in the presence of 100 nM unlabeled 2-oxo-quazepam. The difference between the corrected CPM value obtained in the presence of a known concentration of test drug and the corrected CPM value obtained when no test drug is present in the assay, allows a calculation of the percent inhibition of specific binding for a given test drug concentration. From the values obtained for a number of test drug concentrations, a competitive binding curve may be constructed and an IC50 value calculated. Comparing these results to the binding curve and IC50 value of a known BZ-1 binding compound, such as unlabeled 2-oxo-quazepam, provides valuable information about the relative BZ-1 binding activity of the test drug.

EXAMPLE IV.

Method for Determining the Level of BZ-1 Activity in a Test Sample.

This method is conducted in the same manner as Example III except that various dilutions of a test sample obtained from plasma, serum, urine, saliva or other bodily fluid is substituted for the various concentrations of potential drug. The results will indicate the relative BZ-1 activity of the sample when compared to an appropriate standard. This is a useful diagnostic tool to determine if observed neurological disorders (manifested in BZ-1 active effects on behavior) are the result of the presence of BZ-1 active compounds in the observed patient.

The descriptions of the foregoing embodiments of the invention have been presented for the purpose of illustration and description. They are not intended to be exhaustive or to limit the invention to the actual forms disclosed. Obviously, many modifications and variations are possible in light of the above teachings. The embodiments were chosen and described in order to best explain the principles of the invention and its practical application to enable others skilled in the art to best utilize the invention in various embodiments and with various modifications as are suited to the particular use contemplated.

All references herein disclosed are incorporated by reference for their pertinent teachings.

What is claimed is:

1. A method for analyzing a test compound or test sample for type 1 benzodiazepine receptor binding activity comprising:
    (a) supplying a mammalian brain membrane preparation containing type 1 benzodiazepine receptors;
    (b) adding radioactively labeled 2-oxo-quazepam to said membrane preparation;
    (c) adding a test compound or test sample to said membrane preparation;
    (d) measuring the amount of label complexed with said type 1benzodiazepine receptors; and
    (e) comparing the amount of label measured in step (d) with results obtained from a standard binding curve, thereby analyzing the test compound or test sample for type 1 benzodiazepine receptor binding activity.

2. The method of claim 1 wherein said test sample is selected from the group consisting of an aqueous solution, saliva, serum and urine.

3. The method of claim 1 wherein said mammalian brain membrane preparation is from a rat brain.

4. The method of claim 3 wherein said brain membrane preparation is from brain cortex tissue.

5. A kit for determining the level of type 1 benzodiazepine receptor binding activity of an anxiolytic drug in a test sample, said kit comprising:
    (a) a mammalian brain membrane preparation containing type 1 benzodiazepine receptors; and
    (b) a sufficient amount of radioactively labeled 2-oxo-quazepam to determine the level of type 1 benzodiazepine receptor binding activity of an anxiolytic drug in a test sample.

6. The kit of claim 5 wherein the labeled 2-oxo-quazepam is comprised of tritium ($^3$H) atoms.

7. The kit of claim 6 wherein the labeled 2-oxo-quazepam is comprised of tritium ($^3$H) atoms located on the α-carbon of the trifluoroethyl substituent located at the #1 position.

8. The kit of claim 5 wherein said brain membrane preparation is from brain cortex tissue.

9. The kit of claim 5 wherein said mammalian brain membrane preparation is from a rat brain.

10. The kit of claim 6 wherein said brain membrane preparation is from brain cortex tissue.

11. The kit of claim 7 wherein said brain membrane preparation is from brain cortex tissue.

* * * * *